United States Patent [19]
Yoo et al.

[11] Patent Number: 5,885,783
[45] Date of Patent: Mar. 23, 1999

[54] AUTOIMMUNE INNER EAR DISEASE ANTIGEN AND DIAGNOSTIC ASSAY

[76] Inventors: Tai-June Yoo, 7328 Cotton Plant Cove, Memphis, Tenn. 38119; Kuang-Chaun Cheng, 1814 Teddington Dr., Germantown, Tenn. 38138

[21] Appl. No.: 886,751

[22] Filed: Jul. 2, 1997

[51] Int. Cl.$^6$ ........................ G01N 33/68; G01N 33/564; C07K 7/08; C07K 14/435
[52] U.S. Cl. .......................... 435/7.1; 435/7.92; 435/960; 435/810; 436/506; 530/326; 530/350
[58] Field of Search ................................ 435/6, 7.1, 7.92, 435/960, 810; 436/506; 530/326, 350

[56] References Cited

U.S. PATENT DOCUMENTS

| | | | |
|---|---|---|---|
| 5,582,995 | 12/1996 | Avruch | 435/71 |
| 5,618,670 | 4/1997 | Rapp | 435/6 |

FOREIGN PATENT DOCUMENTS

WO 94/29727  12/1994  WIPO .

OTHER PUBLICATIONS

Blagosklonny M, et al., Proc. Am Assoc. Cancer Res., 37:13, Abstr. #88, Apr. 20, 1996.
Jasti, RK, et al., Proc. Am. Assoc. Cancer Res. 37:605, Abstr. #4147, Apr. 20, 1996.
Alberts, B, et al., Molecular Biology of the Cell, Second Ed. Garland Publishing, Inc. pp. 1205–1212, 1989.
Soliman AM, Acta Otolaryngol. (Stockh), 117:501–504, 1997.
Yoo, TJ, et al., Science, 217:1153–1155, 1982.
Arenberg, IK, et al., Surgery of the Inner Ear, Proc. Third Int'l Symp. Workshop Surg Inner Ear, pp. 31–52, Jul. 29, 1990.
Harada, T, Ann. Otol. Rhinol. Laryngol. 101:72–77, Nov. 2, 1992.
Barna BP and Hughes GB, Progress Controvers. Autoimmune Dis. Test. 17:581–594, Oct. 2, 1997.
Fattori B, Laryngoscope 104:1290–1294, Oct. 18, 1994.
BioRad Protein Blotting: A Guide to Transfer and Detection, Second Edition, Bulletin 1721 US/EG Rev B, Dec. 27, 1996.
Gottschlich S, et al., Laryngoscope, 105:1347–1352, Dec. 13, 1995.
"Allergic and immunologic aspects of Meniere's disease"; M. Jennifer Derebery, M.D.; *Otolaryngology—Head and Neck Surgery*; Mar. 1996; pp. 360–365.
"A Subpopulation of Meniere's Patients Produce Antibodies Bind to Endolymphatic Sac Antigens"; Ahmed M. Soliman; *The American Journal of Otology;* vol. 17, No. 1; 1996; pp. 76–80.
"Antibodies against Inner–Ear Proteins in the Sera of Patients with Inner–Ear Diseases"; T.J. Yoo, MD, PhD; *S. Karger AG, Basel;* ORL 1997; 59:10–17.
"Inner Ear Antoantibodies in Patients With Rapidly Progressive Sensorineural Hearing Loss"; Jeffrey P. Harris, MD, PhD et al;*Laryngoscope 100;* May 1990, pp. 516–524.
Antibodies Against A 30 Kilodalton Cochlear Protein and Type II and IX Collagens in the Serum of Patients With Inner Ear Disease; Thomas Joliat, MD et al.; *Ann Otol Rhinol Laryngol* 101:1992; pp. 1000–1006.
Guinea Pig Inner Ear Antigens: Extraction and Application to the Study of Human Autoimmune Inner Ear Disease; M.Y. Cao, MD et al.; *Laryngoscope* 106: Feb. 1996; pp. 207–212.

*Primary Examiner*—Christina Y. Chan
*Assistant Examiner*—Mary B. Tung
*Attorney, Agent, or Firm*—Jones & Askew, LLP

[57] ABSTRACT

A 28 kD antigen present in the membranous structure of the inner ear and an immunoassay method for diagnosing Meniere's disease using the 28 kD antigen as a target substance for detecting target binding substance in biological fluid from an animal or human having symptoms of a disease of the inner ear.

8 Claims, 3 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( v i ) ORIGINAL SOURCE:
        ( A ) ORGANISM: Guinea Pig     ( i x ) FEATURE:
        ( A ) NAME/KEY: Peptide
        ( B ) LOCATION: 1..19
        ( D ) OTHER INFORMATION: /note= "Guinea Pig Raf-1"

( x i ) SEQUENCE DESCRIPTION: SEQ ID NO:1:

```
Ile Val Gln Gln Phe Gly Phe Gln Arg Arg Ala Ser Asp Asp Gly Lys
1               5                   10                  15

Leu Thr Gln
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( v i ) ORIGINAL SOURCE:
        ( A ) ORGANISM: Homo sapiens     ( i x ) FEATURE:
        ( A ) NAME/KEY: Peptide
        ( B ) LOCATION: 1..19
        ( D ) OTHER INFORMATION: /note= "Human Raf-1"

( x i ) SEQUENCE DESCRIPTION: SEQ ID NO:2:

```
Ile Val Gln Gln Phe Gly Tyr Gln Arg Arg Ala Ser Asp Asp Gly Lys
1               5                   10                  15

Leu Thr Asp
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear    ( i i ) MOLECULE TYPE: peptide  ( i i i ) HYPOTHETICAL: NO   ( i v ) ANTI-SENSE: NO    ( v i ) ORIGINAL SOURCE:
        ( A ) ORGANISM: Chicken    ( i x ) FEATURE:
        ( A ) NAME/KEY: Peptide
        ( B ) LOCATION: 1..19
        ( D ) OTHER INFORMATION: /note= "Chicken Raf-1"

( x i ) SEQUENCE DESCRIPTION: SEQ ID NO:3:

```
Ile  Val  Gln  Gln  Phe  Gly  Tyr  Gln  Arg  Arg  Ala  Ser  Asp  Asp  Gly  Lys
 1                   5                        10                       15

Ile  Ser  Asp
```

( 2 ) INFORMATION FOR SEQ ID NO:4:

( i ) SEQUENCE CHARACTERISTICS:
        ( A ) LENGTH: 148 amino acids
        ( B ) TYPE: amino acid
        ( C ) STRANDEDNESS: single
        ( D ) TOPOLOGY: linear    ( i i ) MOLECULE TYPE: peptide  ( i i i ) HYPOTHETICAL: NO   ( i v ) ANTI-SENSE: NO     ( v ) FRAGMENT TYPE: N-terminal    ( v i ) ORIGINAL SOURCE:
        ( A ) ORGANISM: Homo sapiens    ( x i ) SEQUENCE DESCRIPTION: SEQ ID NO:4:

```
Met  Glu  His  Ile  Gln  Gly  Ala  Trp  Lys  Thr  Ile  Ser  Asn  Gly  Phe  Gly
 1                   5                        10                       15

Phe  Lys  Asp  Ala  Val  Phe  Asp  Gly  Ser  Ser  Cys  Ile  Ser  Pro  Thr  Ile
                20                        25                       30

Val  Gln  Gln  Phe  Gly  Tyr  Gln  Arg  Arg  Ala  Ser  Asp  Asp  Gly  Lys  Leu
           35                        40                       45

Thr  Asp  Pro  Ser  Lys  Thr  Ser  Asn  Thr  Ile  Arg  Val  Phe  Leu  Pro  Asn
           50                        55                       60

Lys  Gln  Arg  Thr  Val  Val  Asn  Val  Arg  Asn  Gly  Met  Ser  Leu  His  Asp
 65                        70                       75                        80

Cys  Leu  Met  Lys  Ala  Leu  Lys  Val  Arg  Gly  Leu  Gln  Pro  Glu  Cys  Cys
                85                        90                       95

Ala  Val  Phe  Arg  Leu  Leu  His  Glu  His  Lys  Gly  Lys  Lys  Ala  Arg  Leu
               100                       105                      110

Asp  Trp  Asn  Thr  Asp  Ala  Ala  Ser  Leu  Ile  Gly  Glu  Glu  Leu  Gln  Val
               115                       120                      125

Asp  Phe  Leu  Asp  His  Val  Pro  Leu  Thr  Thr  His  Asn  Phe  Ala  Arg  Lys
               130                       135                      140
```

```
            Thr  Phe  Leu  Lys
            1 4 5
```

( 2 ) INFORMATION FOR SEQ ID NO:5:

( i ) SEQUENCE CHARACTERISTICS:
        ( A ) LENGTH: 217 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: internal     ( v i ) ORIGINAL SOURCE:
        ( A ) ORGANISM: Homo sapiens     ( x i ) SEQUENCE DESCRIPTION: SEQ ID NO:5:

```
Gly  Phe  Arg  Cys  Gln  Thr  Cys  Gly  Tyr  Lys  Phe  His  Glu  His  Cys  Ser
1                  5                        10                       1 5

Thr  Lys  Val  Pro  Thr  Met  Cys  Val  Asp  Trp  Ser  Asn  Ile  Arg  Gln  Leu
                2 0                2 5                          3 0

Leu  Leu  Phe  Pro  Asn  Ser  Thr  Ile  Gly  Asp  Ser  Gly  Val  Pro  Ala  Leu
          3 5                      4 0                     4 5

Pro  Ser  Leu  Thr  Met  Arg  Arg  Met  Arg  Glu  Ser  Val  Ser  Arg  Met  Pro
          5 0                5 5                      6 0

Val  Ser  Ser  Gln  His  Arg  Tyr  Ser  Thr  Pro  His  Ala  Phe  Thr  Phe  Asn
6 5                      7 0                     7 5                       8 0

Thr  Ser  Ser  Pro  Ser  Ser  Glu  Gly  Ser  Leu  Ser  Gln  Arg  Gln  Arg  Ser
                8 5                     9 0                       9 5

Thr  Ser  Thr  Pro  Asn  Val  His  Met  Val  Ser  Thr  Thr  Leu  Pro  Val  Asp
                1 0 0                  1 0 5                     1 1 0

Ser  Arg  Met  Ile  Glu  Asp  Ala  Ile  Arg  Ser  His  Ser  Glu  Ser  Ala  Ser
          1 1 5                 1 2 0                     1 2 5

Pro  Ser  Ala  Leu  Ser  Ser  Ser  Pro  Asn  Asn  Leu  Ser  Pro  Thr  Gly  Trp
     1 3 0                1 3 5                     1 4 0

Ser  Gln  Pro  Lys  Thr  Pro  Val  Pro  Ala  Gln  Arg  Glu  Arg  Ala  Pro  Val
1 4 5                     1 5 0                     1 5 5                      1 6 0

Ser  Gly  Thr  Gln  Glu  Lys  Asn  Lys  Ile  Arg  Pro  Arg  Gly  Gln  Arg  Asp
                1 6 5                     1 7 0                     1 7 5

Ser  Ser  Tyr  Tyr  Trp  Glu  Ile  Glu  Ala  Ser  Glu  Val  Met  Leu  Ser  Thr
               1 8 0                    1 8 5                     1 9 0

Arg  Ile  Gly  Ser  Gly  Ser  Phe  Gly  Thr  Val  Tyr  Lys  Gly  Lys  Trp  His
          1 9 5                      2 0 0                    2 0 5

Gly  Asp  Val  Ala  Val  Lys  Ile  Leu  Lys
          2 1 0                2 1 5
```

( 2 ) INFORMATION FOR SEQ ID NO:6:

( i ) SEQUENCE CHARACTERISTICS:
        ( A ) LENGTH: 648 amino acids
        ( B ) TYPE: amino acid
        ( C ) STRANDEDNESS: single
        ( D ) TOPOLOGY: linear     ( i i ) MOLECULE TYPE: protein     ( i i i ) HYPOTHETICAL: NO (iv) ANTI-SENSE: NO (v) FRAGMENT TYPE: N-terminal (vi) ORIGINAL SOURCE:
  (A) ORGANISM: Homo sapiens (xi) SEQUENCE DESCRIPTION: SEQ ID NO:6:

```
Met Glu His Ile Gln Gly Ala Trp Lys Thr Ile Ser Asn Gly Phe Gly
 1               5                  10                  15

Phe Lys Asp Ala Val Phe Asp Gly Ser Ser Cys Ile Ser Pro Thr Ile
                20              25                  30

Val Gln Gln Phe Gly Tyr Gln Arg Arg Ala Ser Asp Asp Gly Lys Leu
            35              40              45

Thr Asp Pro Ser Lys Thr Ser Asn Thr Ile Arg Val Phe Leu Pro Asn
    50              55                          60

Lys Gln Arg Thr Val Val Asn Val Arg Asn Gly Met Ser Leu His Asp
65              70                  75                      80

Cys Leu Met Lys Ala Leu Lys Val Arg Gly Leu Gln Pro Glu Cys Cys
                85              90                      95

Ala Val Phe Arg Leu Leu His Glu His Lys Gly Lys Lys Ala Arg Leu
            100             105                 110

Asp Trp Asn Thr Asp Ala Ala Ser Leu Ile Gly Glu Glu Leu Gln Val
        115             120                 125

Asp Phe Leu Asp His Val Pro Leu Thr Thr His Asn Phe Ala Arg Lys
    130             135                 140

Thr Phe Leu Lys Leu Ala Phe Cys Asp Ile Cys Gln Lys Phe Leu Leu
145             150             155                         160

Asn Gly Phe Arg Cys Gln Thr Cys Gly Tyr Lys Phe His Glu His Cys
                165             170                     175

Ser Thr Lys Val Pro Thr Met Cys Val Asp Trp Ser Asn Ile Arg Gln
            180             185                 190

Leu Leu Leu Phe Pro Asn Ser Thr Ile Gly Asp Ser Gly Val Pro Ala
        195             200             205

Leu Pro Ser Leu Thr Met Arg Arg Met Arg Glu Ser Val Ser Arg Met
    210             215             220

Pro Val Ser Ser Gln His Arg Tyr Ser Thr Pro His Ala Phe Thr Phe
225             230             235                         240

Asn Thr Ser Ser Pro Ser Ser Glu Gly Ser Leu Ser Gln Arg Gln Arg
                245             250                 255

Ser Thr Ser Thr Pro Asn Val His Met Val Ser Thr Thr Leu Pro Val
            260             265                 270

Asp Ser Arg Met Ile Glu Asp Ala Ile Arg Ser His Ser Glu Ser Ala
    275             280             285

Ser Pro Ser Ala Leu Ser Ser Ser Pro Asn Asn Leu Ser Pro Thr Gly
    290             295             300

Trp Ser Gln Pro Lys Thr Pro Val Pro Ala Gln Arg Glu Arg Ala Pro
305             310             315                         320

Val Ser Gly Thr Gln Glu Lys Asn Lys Ile Arg Pro Arg Gly Gln Arg
                325             330                 335

Asp Ser Ser Tyr Tyr Trp Glu Ile Glu Ala Ser Glu Val Met Leu Ser
            340             345                 350

Thr Arg Ile Gly Ser Gly Ser Phe Gly Thr Val Tyr Lys Gly Lys Trp
    355             360             365

His Gly Asp Val Ala Val Lys Ile Leu Lys Val Val Asp Pro Thr Pro
    370             375             380
```

-continued

| | | | | | | | | | | | | | | | |
|---|---|---|---|---|---|---|---|---|---|---|---|---|---|---|---|
| Glu 385 | Gln | Phe | Gln | Ala | Phe 390 | Arg | Asn | Glu | Val | Ala 395 | Val | Leu | Arg | Lys | Thr 400 |
| Arg | His | Val | Asn | Ile 405 | Leu | Leu | Phe | Met | Gly 410 | Tyr | Met | Thr | Lys | Asp 415 | Asn |
| Leu | Ala | Ile | Val 420 | Thr | Gln | Trp | Cys | Glu 425 | Gly | Ser | Ser | Leu | Tyr 430 | Lys | His |
| Leu | His | Val 435 | Gln | Glu | Thr | Lys | Phe 440 | Gln | Met | Phe | Gln | Leu 445 | Ile | Asp | Ile |
| Ala | Arg 450 | Gln | Thr | Ala | Gln | Gly 455 | Met | Asp | Tyr | Leu | His 460 | Ala | Lys | Asn | Ile |
| Ile 465 | His | Arg | Asp | Met | Lys 470 | Ser | Asn | Asn | Ile | Phe 475 | Leu | His | Glu | Gly | Leu 480 |
| Thr | Val | Lys | Ile | Gly 485 | Asp | Phe | Gly | Leu | Ala 490 | Thr | Val | Lys | Ser | Arg 495 | Trp |
| Ser | Gly | Ser | Gln 500 | Gln | Val | Glu | Gln | Pro 505 | Thr | Gly | Ser | Val | Leu 510 | Trp | Met |
| Ala | Pro | Glu 515 | Val | Ile | Arg | Met | Gln 520 | Asp | Asn | Asn | Pro | Phe 525 | Ser | Phe | Gln |
| Ser | Asp 530 | Val | Tyr | Ser | Tyr | Gly 535 | Ile | Val | Leu | Tyr | Glu 540 | Leu | Met | Thr | Gly |
| Glu 545 | Leu | Pro | Tyr | Ser | His 550 | Ile | Asn | Asn | Arg | Asp 555 | Gln | Ile | Ile | Phe | Met 560 |
| Val | Gly | Arg | Gly | Tyr 565 | Ala | Ser | Pro | Asp | Leu 570 | Ser | Lys | Leu | Tyr | Lys 575 | Asn |
| Cys | Pro | Lys | Ala 580 | Met | Lys | Arg | Leu | Val 585 | Ala | Asp | Cys | Val | Lys 590 | Lys | Val |
| Lys | Glu | Glu 595 | Arg | Pro | Leu | Phe | Pro 600 | Gln | Ile | Leu | Ser | Ser 605 | Ile | Glu | Leu |
| Leu | Gln 610 | His | Ser | Leu | Pro | Lys 615 | Ile | Asn | Arg | Ser | Ala 620 | Ser | Glu | Pro | Ser |
| Leu 625 | His | Arg | Ala | Ala | His 630 | Thr | Glu | Asp | Ile | Asn 635 | Ala | Cys | Thr | Leu | Thr 640 |
| Thr | Ser | Pro | Arg | Leu 645 | Pro | Val | Phe | | | | | | | | |

AUTOIMMUNE INNER EAR DISEASE ANTIGEN AND DIAGNOSTIC ASSAY

FIELD OF THE INVENTION

This invention relates to the field of immunology and more specifically relates to an antigen of the membranous structures of the inner ear and to an immunoassay method for detecting an autoimmune disease of the membranous structures of the inner ear.

BACKGROUND OF THE INVENTION

Hearing problems can result from a variety of disorders, diseases or traumas of the inner ear. Symptoms of inner ear problems include, but are not limited to, hearing loss, dizziness, vertigo and tinnitus. Several inner ear diseases have recently been classified as autoimmune diseases. These include, but are not limited to, Meniere's disease, progressive bilateral sensorineural hearing loss (PSHL), otosclerosis and sudden hearing loss.

Meniere's disease, although idiopathic by definition, has been ascribed to a variety of causes, among which are autoimmune factors. There is evidence to suggest that antibodies generated against inner ear proteins cause inner ear inflammation and swelling that can result in a complete loss of hearing (Dereby, M. *Otolaryngology-Head & Neck Surgery* 114:360–365, 1996). Symptoms typically associated with Meniere's disease include ringing in the ears, dizziness, a sense of fullness or pressure in the ears, and progressive deafness. These symptoms may be produced by a sudden influx of fluid into the endolymphatic sac, resulting in a rupture of Reisser's membrane in the cochlea. Immunological derangement of the endolymphatic sac or other membranous structures of the inner ear could initiate a cascade of reactions leading to endolymphatic hydrops and presenting as Meniere's disease (Soliman, A. *American Journal of Otology* 17:70–80, 1996). There are at least four million Meniere's disease patients in the United States, and many more patients report symptoms associated with Meniere's disease but cannot be positively diagnosed.

Researchers have attempted to isolate the antigen or antigens responsible for autoimmune inner ear diseases. A protein is considered to be a potential antigen if it is reactive with antibodies produced by patients exhibiting autoimmune inner ear diseases.

For example, antibodies in the sera of patients having inner ear disease have been found to react with protein bands of 58 kD and of 30 kD on Western blots of guinea pig inner ear extracts (Cao, M. et al., *Laryngoscope* 106:207–212, 1996). The 58 kD band was shown to be nonspecific to the inner ear when antibodies reacted with a 58 kD band on Western blots of guinea pig brain, lung and liver. In contrast, the 30 kD band was specific to the inner ear. Antibodies from patients reacted with a 30 kD band on Western blots of extracts from Corti's organ, the spiral ganglion and the acoustic nerve fiber, but not with extracts from the spinal ligament and the stria vascularis.

Antibodies against a 30 kD cochlear protein have been in reported in the serum of some patients with Meniere's disease (Joliat, T. et al., *Ann. Otol. Rhinol. Laryngol.* 101:1001–1006, 1994 and Cao, M. et al., *Laryngoscope* 106:207–212, 1996). This 30 kD protein has been identified as the major peripheral myelin protein "PO" and is believed to be associated with acoustic nerve and spiral ganglion (Cao, M. et al., *Laryngoscope* 106:207–212 (1996). Antibodies reactive with the 30 kD protein are not specific for Meniere's disease as these antibodies have been found in patients having other autoimmune diseases such as progressive bilateral sensorineural hearing loss (PSNHL), otosclerosis and sudden deafness and in control subjects. (Cao, M. et al., IMMUNOBIOLOGY IN OTOLOGY, RHINOLOGY AND LARYNGOLOGY (eds. Mogi, G., Veldman, J., and Kawauchi, H.) Kugler Publ. Amsterdam/N.Y., (1994) pp. 263–268).

Antibodies against a 68 kD protein in extracts from bovine inner ear have been reported in the serum of PSNHL patients (Harris J. and Sharp P. *Laryngoscope* 100:516–524, 1990). This 68 kD protein has been identified as a 70 kD heat shock protein that has been implicated in other autoimmune diseases such as Lyme's disease and ulcerative colitis (Billings P. et al. *Ann. Otol. Rhinol. Laryngol.* 104:181–188, 1995).

An early diagnosis of autoimmune inner ear disease is critical. Prompt treatment of the disease at an early stage of the illness may preserve any remaining inner ear function. Moreover, the ability to distinguish antigenic epitopes of the inner ear relevant to the pathogenesis of specific autoimmune inner ear diseases will enable clinical investigation and research on autoimmune inner ear disease, and will further enable the clinical diagnosis of autoimmune inner ear diseases and immunologic therapy.

As the availability of human inner ear tissue is extremely limited, there is an on-going need for the identification of disease-specific antigens and for the development of simple, sensitive and reproducible assays for the detection and differential diagnosis of autoimmune inner ear diseases.

SUMMARY OF THE INVENTION

An isolated 28 kD antigen present in the membranous structure of the inner ear and an immunoassay method for diagnosing Meniere's disease using the 28 kD antigen as a target substance for detecting target binding substance in biological fluid from an animal or human having symptoms of a disease of the inner ear are provided.

It is an object of the present invention to provide an antigen identified in the membranous structure of the inner ear that reacts specifically with antibodies from the sera of patients having an autoimmune disease of the membranous structures of the inner ear.

It is a further object of the present invention to provide a simple, rapid, sensitive and reproducible method for detecting antibodies to antigens from the membranous structures of the inner ear.

It is a further object of the present invention to provide an isolated antigen from the membranous structures of the inner ear that reacts specifically with antibodies in the sera of patients having Meniere's disease.

It is a further object of the present invention to provide a sensitive blood test for the detection of Meniere's disease in the early stages of the disease.

It is a further object of the present invention to provide an immunoassay that can distinguish Meniere's disease from other autoimmune ear diseases.

It is a further object of the present invention to provide an immunoassay that can monitor the progression of Meniere's disease or the effects of treatment for Meniere's disease.

It is a further object of the present invention to provide an antigen to be used for the immunotherapeutic treatment of Meniere's disease.

These and other objects of the present invention will become apparent after reading the following detailed description of the disclosed embodiments and the appended claims.

DETAILED DESCRIPTION OF THE INVENTION

As used herein, the term "28 kD antigen" refers to a protein extract or peptide from the membranous structures of the inner ear of a mammal, a protein or peptide having the amino acid sequence N'-IVQQFGFQRRASDDGKLTQ-C' (SEQ.ID.NO.:1) and antigenic variants thereof, a protein or peptide having the amino acid sequence N'-IVQQFGYQRRASDDGKLTD-C' (SEQ.ID.NO.:2) and antigenic variants thereof and a recombinant GST-Raf-1 protein or peptide having the amino acid sequence N'-MEHIQGAWKTISNGFGFKDAVFDGSSCISPTIVQQ FGYQRRASDDGKLTDPSKTSNTIRVFLPNKQRTVVN VRNGMSLHDCLMKALKVRGLQPECCAVFRLLHEHK GKKARLDWNTDAASLIGEELQVDFLDHVPLTTHNFA RKTFLK-C' (SEQ.ID.NO.:4) and antigenic variants thereof.

As used herein, the term "target substance" refers to the 28 kD antigen or a nucleic acid molecule having a sequence encoding the 28 kD antigen of the membranous structures of the inner ear of a mammal.

As used herein, the term "immune sample" refers to samples having antibodies that interact specifically with the 28 kD antigen.

As used herein, the term "target-binding substance" refers to immune samples and to biological molecules, such as antibodies, which interact specifically with the 28 kD antigen. The term "target-binding substance" further include nucleic acid probes that hybridize under stringent hybridization conditions to a nucleic acid molecule having a sequence encoding the 28 kD antigen of the membranous structures of the inner ear of a mammal.

As used herein, the term "preimmune sample" refers to samples not having antibodies that interact specifically with the 28 kD antigen.

As used herein, the term "membranous structures" refers to the basilar membrane, organ of Corti, stria vascularis, spiral ligament and vestibular epithelium of the inner ear.

As used herein, the term "neural structures" refers to the spiral ganglion, cochlear nerve in the modiolus and vestibular nerve in the temporal bone of the inner ear.

As used herein, the term "GST-Raf-1" refers to recombinant purified GST-Raf-1 protein (SEQ.ID.NO.:4) of human Raf-1 protein (SEQ.ID.NO.:6). Anti-Raf-1 is obtained from Transduction Laboratories (Lexington Ky.).

The term "antigenic variant" refers to a protein or peptide having an amino acid sequence different from the protein or peptide to which it is compared, but having similar immunologic characteristics such as the ability to bind to one or more antibodies that bind to the protein or peptide to which it is compared.

An antigen and a diagnostic assay method for detecting antibodies to the antigen in a biological sample are described herein. The antigen is the 28 kD antigen, as defined above, and the diagnostic assay method is specific for detecting antibodies to the 28 kD antigen. The 28 kD antigen is present in the membranous fraction of the inner ear, but is not present in the neural fraction of the inner ear, facial nerve or brain tissue (Suzuki et al., *ORL*, 59:10–17, 1997). The 28 kD antigen shows greater than 75% homology with residues 41 to 60 of Raf-1 protein from various species including, but not limited to, the human sequence (SEQ.ID.NO.:2) and the chicken sequence (SEQ.ID.NO.:3).

Preferably, the 28 kD antigen has the sequence of SEQ.ID.NO.:1, SEQ.ID.NO.:2, SEQ.ID.NO.:4 or antigenic variants thereof and reacts with a biological fluid from an individual having an autoimmune disease of the membranous structures of the inner ear. More preferably, the 28 kD antigen has the amino acid sequence of SEQ.ID.NO.:1 or SEQ.ID.NO.:2 or antigenic variants thereof and reacts with a biological fluid from an individual having Meniere's disease. Most preferably, the 28 kD antigen has the amino acid sequence of SEQ.ID.NO.:1 and antigenic variants thereof and reacts with a biological fluid from an individual having Meniere's disease.

The diagnostic assay for detecting the 28 kD antigen of the membranous structures of the inner ear can be, for example, an immunoassay. Such an immunoassay includes, but is not limited to, an ELISA, a Western blot assay, a competitive binding assay, a particle based immunoassay, a dual particle competitive immunoassay, and any of the other immunoassay methods known to those skilled in the art.

For example, in a conventional immunoassay, such as an ELISA, an inert solid-phase material, usually a plastic microtiter plate, is contacted with a solution containing the target substance (28 kD antigen) so that the target substance binds to, or coats, the solid phase material. The bound target substance is then contacted with an aqueous sample obtained from an individual having symptoms of inner ear disease, which may or which may not contain a target-binding substance (anti-28 kD antibody). Unbound target-binding substance is removed, and the amount of reacted target-binding substance is quantitated using any of a number of detection devices known to those skilled in the art. For example, the bound target-binding substance may be detected with a second antibody to which has been attached a detectable label such as an enzyme, radioisotope or fluorescent molecule.

The target substance for use in the present invention includes, but is not limited to, protein extracted from the membranous structures of the inner ear, fractions of protein extracted from the membranous structures of the inner ear, and an isolated 28 kD antigen extracted and purified from the membranous structures of the inner ear. In addition, the target substance for use in the present invention also includes, but is not limited to, a protein or peptide having the amino acid sequence of SEQ.ID.NO.:1 or antigenic variants thereof, a protein or peptide having the amino acid sequence of SEQ.ID.NO.:2 or antigenic variants thereof, and a protein or peptide having the amino acid sequence of SEQ.ID.NO.:4 or antigenic variants thereof obtained using recombinant DNA technology or synthesized by methods known to those skilled in the art of peptide synthesis. It will be understood by those skilled in the art that the term "amino acid sequence of SEQ.ID.NO.:1, 2, or 4" includes antigenic variants thereof.

The concentration of target substance for use in the present invention can range between approximately 1 µg/ml and 100 µg/ml. The more preferable range is between approximately 3 μg/ml and 50 μg/ml. The most preferable range is between approximately 5 μg/ml and 30 μg/ml. The target substance is dissolved in an aqueous solution and can be applied to an inert solid-phase support material by dipping, soaking, coating, spotting, spraying, blotting or other convenient means. Preferred methods include coating, spotting, spraying and blotting. More preferred methods include coating and blotting. For example, in an ELISA, a preferred volume for coating is between about 10 μl/well and 200 μl/well. A more preferred volume for coating is between about 30 μl/well and 150 μl/well. A most preferred volume for coating is between about 50 μl/well and 100 μl/well. Determination of the amount of target substance to be used for each method of application is well within the knowledge of one skilled in the art. For example, a standard target substance, target-binding substance assay combination can be used to determine the amount of target substance to be applied to the inert solid-phase support material.

The solvent for use in the present invention can be any solvent that can solubilize the target-binding substance, and that is sufficiently miscible with water to be completely removed by subsequent thorough rinsing with an aqueous solution. Such solvents include, but are not limited to phosphate buffered saline (PBS), tris(hydroxymethyl)amino methane (TRIS), N-2-hydroxyethylpeperazine-N'-2-ethanesulfonic acid (HEPES), citric acid-phosphate buffer and carbonate buffer. Such aqueous buffers and their appropriate pHs are well known to those skilled in the art. Mixtures of solvents may also be used. Preferred solvents include 0.1M carbonate buffer, pH 9.0, and citric acid-phosphate buffer, pH 5.0. These solvents may contain other chemicals including, but not limited to, SDS, Tween-20, bromphenol blue, glycerol and dithiothreitol.

The solid phase, or inert solid-phase support material, for use in the present invention can be in the form of, but is not limited to, a membrane, a bead, a microtiter plate or any other solid-phase support form known to those skilled in the art. Preferred forms include a membrane strip, a membrane well microtiter plate and a plastic well microtiter plate. More preferred forms include a membrane strip and a plastic well microtiter plate. A most preferred form is a plastic well microtiter plate. In addition, the inert solid-phase support material can be placed into a holder, including but not limited to, a membrane sheet holder, a dot-blot apparatus, a microtiter plate, a column, and a filter. Preferred holders include a membrane sheet holder, a dot-blot apparatus and a microtiter plate.

The blocking buffers for use in the present invention to prevent non-specific binding can be any suitable blocking buffer including, but not limited to, goat serum, fetal calf serum, gelatin, low fat milk, and Tween-20 at various dilutions in an aqueous solution.

The washing solution for use in the present invention can be any suitable aqueous buffer including, but not limited to, phosphate buffered saline (PBS), tris(hydroxymethyl)amino methane (TRIS) and N-2-hydroxy-ethylpeperazine-N'-2-ethanesulfonic acid (HEPES). Such aqueous buffers and their appropriate pHs are well known to those skilled in the art.

The target-binding substance for use in the present invention is a substance which binds specifically to the target substance. Examples of target-binding substances include, but are not limited to, antibodies. Preferred target-binding substances are antibodies to proteins of the membranous structures of the inner ear. More preferred target-binding substances are antibodies to a 28 kD antigen of the membranous structure of the inner ear in serum from individuals having inner ear disease. Most preferred target-binding substances are antibodies to a 28 kD protein of the membranous structure of the inner ear in the serum of individuals having Meniere's disease.

Any convenient indicator method can be used to detect binding of a target-binding substance to a target substance. Such methods include, but are not limited to, the use of enzymes, enzyme cofactors, enzyme effectors, chromogenic substances, fluorogenic substances, chemiluminescent substances, bioluminescent substances, and labeled antibodies. Preferred indicator methods are the peroxidase-labeled antibody method and the alkaline phosphatase-labeled antibody method.

The present invention further comprises an assay kit for detecting target-binding substance in a biological sample comprising an inert solid-phase support material having target-binding substance immobilized thereon and may further contain reagents and a holder for the inert solid-phase support material. The kit may additionally contain equipment for safely containing the samples, a vessel for containing the reagents, a timing means, and a colorimeter, reflectometer, or standard against which a color change may be measured. The reagents, including the target substance coated particle and the detectable particle are preferably lyophilized. Most preferably, the coated particle, and the detectable particle are provided in lyophilized form in a single container.

For example, an immunoassay kit useful for measuring the target-binding substance in a biological sample can involve a "sandwich immunoassay". The kit contains a particle coated on its surface with the binding substance, a detectable particle capable of binding to the target-binding substance and a porous membrane having a pore size that prevents passage of the coated particle and allows passage of the detectable particle. The first step in the immunoassay is a binding step, and the second step is a detection step.

In the binding step, a solid phase particle or sphere coated with the target substance is combined in a solution with a sample containing the target-binding substance and reacted for a sufficient amount of time to allow the target substance and the target binding substance to interact. In the detection step, a detectable particle, such as a colored bead, coated with a substance that binds readily to the target-binding substance, such as protein A, protein G, a second antibody reactive to the target-binding substance, or a small synthetic affinity ligand is added to the suspension. The detectable particle binds to the target-binding substance complexed to the target substance coated particle. The reaction mixture is then placed on a membrane having a pore size of sufficient dimension to exclude passage of target substance coated particle which have bound target-binding substance and, therefore, bound detectable particle. Those components which are complexed as target substance particle plus target-binding substance plus detectable particle are retained on the membrane while the other components pass through the pores.

The complex is detected either visually with the naked eye or using a conventional detector, such as a colorimeter or reflectometer, well known to those skilled in the art. In this sandwich immunoassay, the presence of detectable particles indicates the presence of target-binding substance in the sample.

The 28 kD antigen and the immunoassay method and kit described above will be further understood with reference to the following examples, which are in no way intended to limit the scope of the present invention.

EXAMPLE 1

Isolation and Identification of 28 kD Protein from the Membranous Fraction of Retrocochlear Tissue Protein Extraction Proteins are extracted from the membranous fraction of retrocochlear tissue in accordance with the method of Suzuki, M. et al. *ORL,* 59:10–17, 1997 as follows. Briefly, forty Harley strain male guinea pigs (Sasco Co., Wilmington, Mass.) are anesthetized by intraperitoneal injection of a mixture of ketamine (70 mg/kg) and xylazine (70 mg/kg) and perfused with 0.01M phosphate buffered saline (PBS), pH 7.4, through the left ventricle. Both temporal bones are removed and placed in crushed ice.

The membranous portion of the inner ear, including basilar membrane, organ of Corti, stria vascularis, spiral ligament and vestibular epithelium are dissected under a microscope. The neural portion of the inner ear, including the spiral ganglion, cochlear nerve in the modiolus, and vestibular nerve in the temporal bone, the facial nerve and brain tissue are dissected under a microscope.

The membranous tissue and the neural tissue are each sonicated for 20 seconds in lysis buffer (100 mM NaCl, 10 mM Tris buffer (Sigma Chemical Company, St. Louis, Mo.), pH 7.6; 1 mM ethylenediaminetetraacetate (EDTA; Sigma Chemical Company, St. Louis, Mo.), pH 8.0; a surfactant including, but not limited to 0.1% sodium dodecyl sulfate (SDS, Sigma Chemical Company, St. Louis, Mo.) and 1% Nonidet P-40 (Sigma Chemical Company, St. Louis, Mo.); 2 µg/ml aprotinin; and, 100 mg/ml phenylmethysulfonyl fluoride (PMSF, Sigma Chemical Company, St. Louis, Mo.). The extracted membranous proteins and the extracted neural proteins are incubated at 0° C. for 30 minutes and centrifuged at 10,000 rpm for 10 minutes. Each supernatant is filtered through a 0.22 m filter (Millipore Co., Bedford, Mass.), boiled for five minutes in a boiling water bath and stored at –80 C.

Protein concentration is determined after electrophoresis in one-dimensional 12% SDS-polyacrylamide gels (SDS-PAGE) using molecular weight standards (Life Technology, Inc., Grand Island, N.Y.). A range of 1 µg/ml to 10 µg/ml of standard is loaded on the same gel and is compared with inner ear protein extract and with Raf-1 protein.

SDS-Polyacrylamide Gel Electrophoresis (SDS-PAGE)

Samples are fractionated by SDS-PAGE using a 12% running gel and a 5% stacking gel in accordance with the method of Laemmeli et al. Samples of membranous proteins, of neural proteins and of Raf-1 protein are each mixed 1:1 with 100 mM Tris, pH 6.8, 4% SDS, 0.2% bromphenol blue, 20% glycerol and 200 mM dithiothreitol and heated at 100° C. for three minutes. The gels are electrophoresed in a vertical electrophoresis apparatus (Life Technologies, Inc., Grand Island, N.Y.) at 90 volts for seven hours. The gels are fixed and stained with Coomassie brilliant blue (BioRad, Melville, N.Y.) and are destained with 45% methanol, 10% acetic acid and 45% distilled water. Apparent molecular weights of the separated components are calculated by comparison with prestained molecular weight markers (Life Technologies, Inc., Grand Island, N.Y.) electrophoresed in the same gel.

Western Blotting

Proteins, separated in 12% one-dimensional SDS-PAGE as described above, are electroblotted onto polyvinylidene difluoride (PVDF) membrane (BioRad, Melville, N.Y.) using a BioRad Semi-Dry TRANSBLOT CELL membrane (BioRad, Melville, N.Y.) for 1 hour. The PVDF membrane is washed one time with 20 mM Tris, pH 7.5, 500 mM NaCl containing 0.025% Tween-20 (TTBS).

Amino Acid Sequencing

Samples separated in SDS-PAGE and are electroblotted onto PVDF membrane as described above. The band corresponding to the molecular weight of 28 kD is excised from the PVDF membrane and is microsequenced using automated Edman degradation (Applied Biosystems, Ragweed City, Calif.). Nineteen amino acids, having the sequence N'-IVQQFGFQRRASDDGKLTQ-C' (SEQ.ID.NO.:1), are identified with an initial yield of approximately 78.6 picomoles.

Sequence comparison with the Swiss Protein Database shows the microsequence of the 28 kD membranous inner ear protein to have 89.5% identity, 19 amino acid overlap, with residues 41–60 of human Raf-1 protein (SEQ.ID.NO.:2) and 78.9% identity with residues 41–60 of chicken Raf-1 protein (SEQ.ID.NO.:3) as shown in Table 1.

TABLE 1

The 28 kD protein microsequence from guinea pig inner ear and residues 41–60 of Raf-1 protein from human and chicken

| Amino Acid | 40 | 50 | Identity |
|---|---|---|---|
| 28 kD protein | IVQQFGFQR | RASDDGKLTQ | |
| Human Raf-1 | ...... Y.. | ......... D. | 89.5% |
| Chick Raf-1 | ...... Y.. | ........ ISD | 78.9% |

EXAMPLE 2

Preparation of Recombinant GST-Raf-1

A glutathione-s-transferase (GST)-Raf-1 construct, N-domain with residues of 1–148, (SEQ.ID.NO.:4) is provided by Dr. Mark Marshall (Indiana University, Indiana). An overnight culture is diluted 1:100 in fresh LB medium containing 100 µg/ml ampicillin and grown at 37° C. to an $OD_{600}$ of 0.5. The culture is equilibrated to 30° C. and 1 mM isopropyl-beta-D-thiogalacto-pyranoside (Sigma Chemical Co., St. Louis, Mo.) is added to induce GST-Raf-1 expression. After three hours of induction, the cells are pelleted, resuspended in PBS buffer, and incubated overnight at –70° C. The lysate is sonicated and the clear lysate is tumbled with glutathione-SEPHAROSE resin beads (Pharmacia Biotech Inc., Piscataway, N.J.) for 30 minutes. The beads are washed four times with PBS and the GST-Raf-1 fusion protein is eluted with 10 mM reduced glutathione at pH 8.0. The GST-Raf-1 fusion protein is dialyzed against Tris-HCl buffer, pH 8.0, aliquoted, snap frozen, and stored at –80° C. The purity and concentration of the GST-Raf-1 fusion protein is determined by 12% SDS-PAGE.

EXAMPLE 3

Western Blot Immunochemistry Of Sera From Patients With Inner Ear Disease

Proteins are extracted from the guinea pig inner ear, separated in SDS-PAGE and electroblotted onto PVDF membrane as in Example 1. The PVDF membranes are washed one time with TTBS.

Sera from patients with various inner ear diseases, including Meniere's disease, (experimental sera) are provided by Drs. J. Bernstein (Department of Otolaryngology, State University of New York, Buffalo, N.Y.) and Y, Yazawa (Department of Otolaryngology, Shiga University of Medical Science, Seta, Japan). The diagnosis of Meniere's disease is based on the AAO-HNS criteria. Sera from patients with no inner ear diseases (control sera) is obtained from age matched patients. Sera are stored at –20° C.

For use with serum as target binding substance (1st antibody), nonspecific binding is blocked using 25% goat serum in TTBS containing 0.02% sodium azide for one hour at room temperature. The PVDF membrane is incubated in serum diluted 1:50 in TTBS containing 25% goat serum and 0.02% sodium azide overnight at room temperature. The membrane is then washed three times in TTBS and incubated with peroxidase conjugated goat anti-human polyvalent immunoglobulin (Accurate Chemical and Scientific Corp., Westbury, N.Y.) diluted 1:2,000 for two hours at room temperature. The PVDF membrane is washed twice with TTBS for ten minutes at room temperature. Immunoreactive bands are visualized using 0.05M Tris-HCl, pH 7.6, containing 0.02% 3,3'-diaminobenzidine (Chemicon International, Inc. Temecula, Calif.) and 0.01% hydrogen peroxide.

As shown in Table 2, with 24 (53%) of 45 patients with various inner ear diseases show a positive Western blot, whereas 0 of 10 (0%) control patients show a positive Western blot. Of 25 patients with Meniere's disease, 15 (60%) show positive Western blots.

TABLE 2

Patients' diagnoses and Western blot immunochemistry of guinea pig inner ear protein probed from patients with various inner ear diseases.

| | | Positive Western blot | |
|---|---|---|---|
| | n | n | % |
| Meniere's disease | 25 | 15 | 60 |
| Otosclerosis | 6 | 3 | 50 |
| Hearing loss and tinnitus (diagnosis undetermined) | 6 | 3 | 50 |
| PSNHL | 2 | 2 | 100 |
| Cogan's syndrome | 1 | 0 | 0 |
| Sudden deafness | 1 | 0 | 0 |
| Strial atrophy | 2 | 0 | 0 |
| Hereditary hearing loss | 1 | 0 | 0 |
| Syphilitic labyrinthitis | 1 | 1 | 100 |
| Control | 10 | 0 | 0 |

Among the 10 positively reactive bands detected, a 28 kD band is the most common positive band found in sera from Meniere's disease patients with 7 out of 25 sera reactive.

As shown in Table 3, of 24 patients who show a least one positively reactive band, 10 show a positive reaction only in the membranous part, 1 only in the neural part and 13 in both parts.

TABLE 3

As shown in Table 3, of 24 patients who show a least one positively reactive band, 10 show a positive reaction only in the membranous part, 1 only in the neural part and 13 in both parts.
Differences in Western blotting results between the membranous part and the neural part of the inner ear.

| | 25 kD | 28 kD | 30 kD | 32 kD | 40 kD | 42 kD | 46 kD | 52 kD | 67 kD | 79 kD |
|---|---|---|---|---|---|---|---|---|---|---|
| Membranous part | 4 | 9 | 1 | 1 | 1 | 2 | 1 | 7 | 6 | 2 |
| Neural part | 0 | 0 | 2 | 1 | 1 | 2 | 1 | 6 | 4 | 0 |

The marked difference between the two parts of the inner ear is the 28 kD band which is detected only on the membranous part.

EXAMPLE 4
Presence of GST-Raf-1 (SEQ.ID.NO.:4) In Neural Inner Ear Proteins, Facial Nerve Proteins and Brain Tissue Proteins extracted from the membranous portion of the inner ear, the neural portion of the inner ear, the facial nerve and the brain are electrophoresed and electroblotted onto PVDF membrane as in Example 1.

Anti-Raf-1 specific monoclonal antibody is obtained from Transduction Laboratories (Lexington, Ky.). This anti-Raf-1 recognizes amino acids 162–378 of human Raf-1 protein (SEQ.ID.NO.:5). For use with anti-Raf-1 as target-binding substance (1st antibody), nonspecific binding is blocked using 5% nonfat dry milk in 10 mM Tris, pH 7.5, 100 mM NaCl and 0.1% TWEEN-20 surfactant for one hour at room temperature. The PVDF membrane is incubated in anti-Raf-1 diluted 1:1000 in 5% nonfat dry milk in 10 mM Tris, pH 7.5, 100 mM NaCl and 0.1% Tween-20 overnight at room temperature. The membrane is then washed three times in TTBS and incubated with peroxidase-conjugated goat anti-mouse IgG (Sigma Chemical Co., St. Louis, Mo.). Immunoreactive bands are visualized using 0.05M Tris-HCl, pH 7.6, containing 0.02% 3,3'-diamino-benzidine (Chemicon International, Inc., Temecula, Calif.) and 0.01% hydrogen peroxide.

Figure 1:
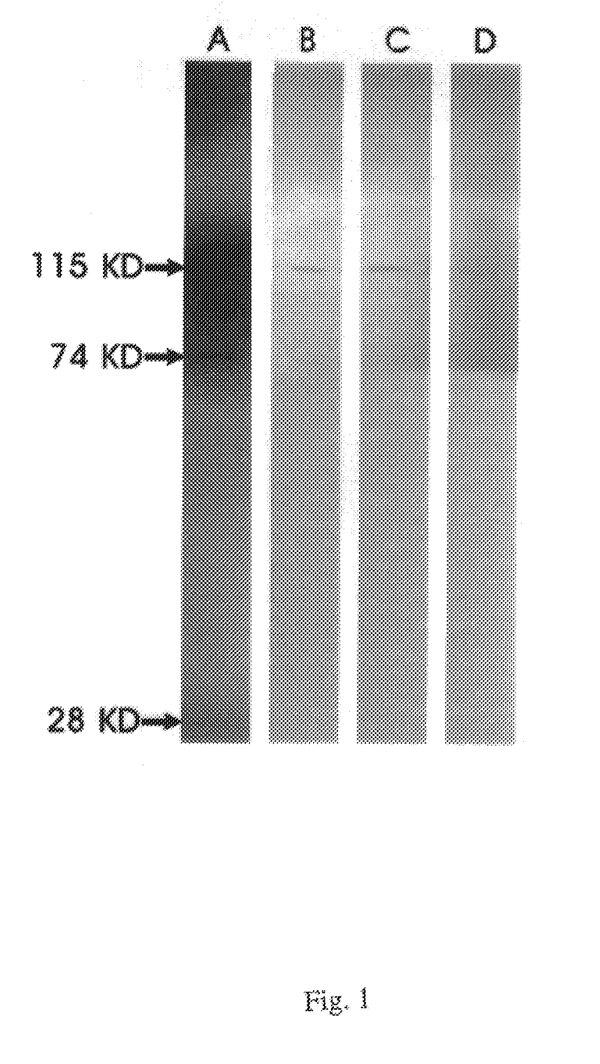
FIG. 1 is a Western blot demonstrating that GST-Raf-1 (SEQ.ID.NO.:4) is present in the membranous portion of the inner ear, but is not present in the neural portion of the inner ear, in facial nerve or in brain tissue.

Anti-Raf-1 monoclonal antibody recognizes 115 kD and 74 kD proteins in extracts from the membranous portion of the inner ear (FIG. 1, Col. A), the neural portion of the inner ear FIG. 1, Col. B), the facial nerve (FIG. 1, Col. C) and the brain (FIG. 1, Col. D). In contrast, anti-Raf-1 monoclonal antibody recognizes the 28 kD protein (SEQ.ID.NO.:1) in extracts from the membranous portion of the inner ear, but not in extracts from the neural portion of the inner ear, the facial nerve and the brain.

EXAMPLE 5
Determination of Raf-1 Antibodies in Sera From Meniere's Patients

Proteins extracted from the membranous portion of the inner ear and recombinant GST Raf-1 protein are electrophoresed in SDS-PAGE and electroblotted onto PVDF membrane as in Example 1 for immunochemical analysis as in Example 3.

Sera from patients with symptomatic Meniere's disease are provided by Drs. J. Bernstein (Department of Otolaryngology, State University of New York, Buffalo, N.Y.) and Y, Yazawa (Department of Otolaryngology, Shiga University of Medical Science, Seta, Japan). The diagnosis of Meniere's disease is based on the AAO-HNS criteria. Sera are stored at −20° C.

Figure 2:
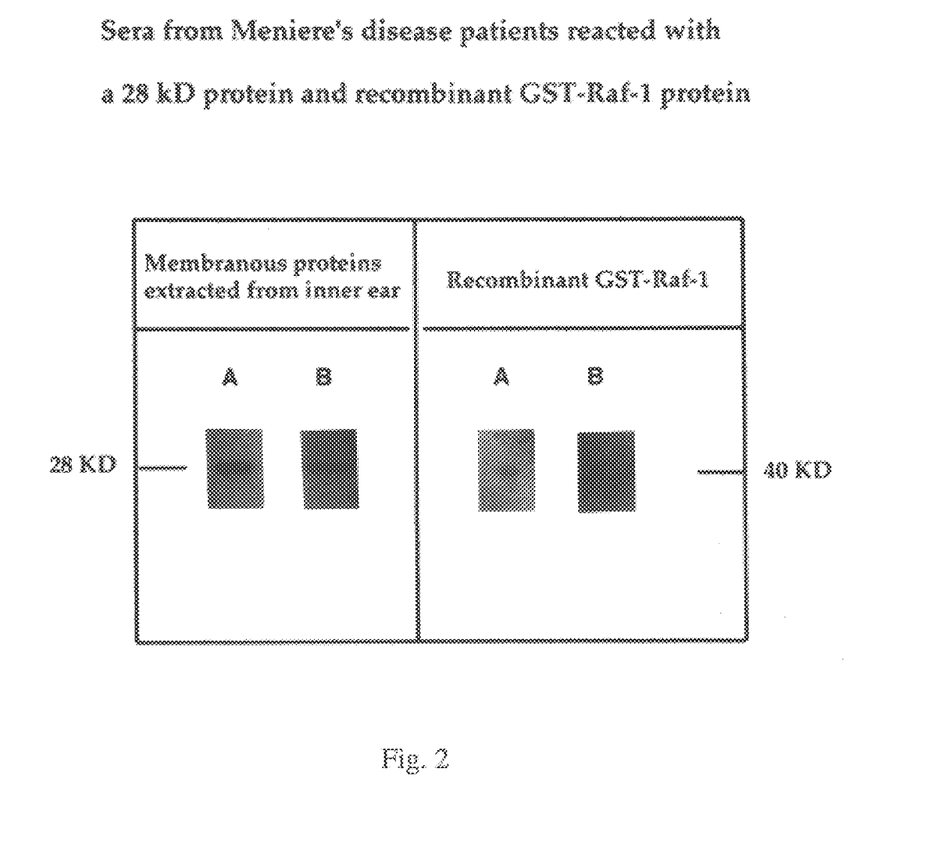
FIG. 2 is a Western blot demonstrating the reactivity of sera from Meniere's disease patients with the 28 kD protein SEQ.ID.NO.:1, (left panel) and with GST-Raf-1, SEQ.ID.NO.:4, (right panel).

FIG. 2A shows that sera from Meniere's disease patients reacts with the 28 kD antigen (SEQ.ID.NO.:1) extracted from the membranous portion of the inner ear of the guinea pig. FIG. 2B shows that sera from the same Meniere's disease patients reacts with the 40 kD recombinant GST-Raf-1 (SEQ.ID.NO.:4).

EXAMPLE 6
Reactivity of Sera From Meniere's Disease Patients with GST Raf-1 (SEQ.ID.NO.:4)

Sera from 27 Meniere's disease patients, provided as in Example 5, are assayed for antibodies against GST-RAF-1 (SEQ.ID.NO.:4) in ELISA.

One hundred microliters of GST-Raf-1 (SEQ.ID.NO.:4) containing 5 μg/μl in 0.1M carbonate buffer, pH 9.6, are dispensed into each well of a polystyrene microtiter plate (Costa, Cambridge, Mass.) and incubated overnight at 4° C. The antigen coated plates are washed three times in PBS-0.05% Tween buffer and incubated with patient's sera (1:40, 1:80, or 1:160 dilution) or with 0.1M carbonate buffer, pH 9.6, as a control, overnight at 4° C. The plates are washed five times with PBS-0.05% Tween buffer and incubated overnight with c-chain specific anti human IgG antibodies (Sigma chemical Co., St. Louis, Mo.) at 4° C. The plates are washed five times in PBS-0.05% Tween buffer and citric acid-phosphate buffer, pH 5.0, containing 0.15 mg/ml of o-phenylenediamine (Sigma Chemical Co., St. Louis, Mo.) is added. The color is developed at room temperature and the reaction is stopped by 2.5M sulfuric acid. The color is measured at 492 nm.

Figure 3:
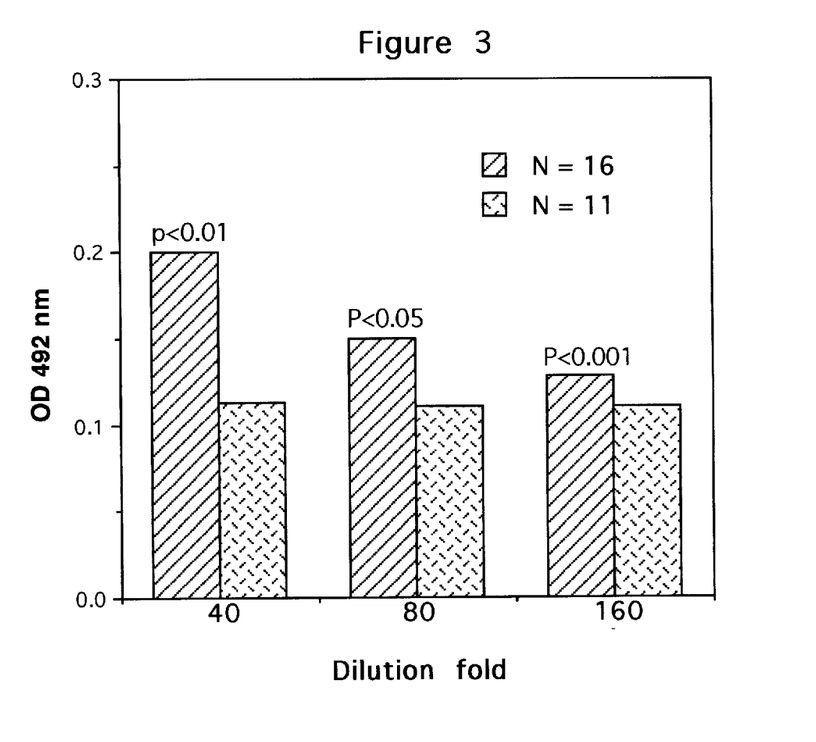
FIG. 3 is a summary of ELISA results demonstrating the reactivity of sera from Meniere's disease patients with GST-Raf-1 (SEQ.ID.NO.:4).

As shown in FIG. 3, 16 of 27 sera obtained from Meniere's patients (59%) recognize GST-Raf-1 (SEQ.ID.NO.:4) in ELISA at dilutions of 1:40, 1:80 and 1:160. Seven of these sera are tested in Western blot analysis and show positive reactivity with the 28 kD band in membranous inner ear extracts of the guinea pig.

While the foregoing specification teaches the principles of the present invention, with examples provided for the purpose of illustration, it will be understood that the practice of the invention encompasses all of the usual variations, adaptation, modification or deletions as come within the scope of the following claims and their equivalents.

We claim:

1. A method aiding in the detection of Meniere's disease in a human or animal comprising:
   (a) incubating a biological sample from the animal or human with an isolated antigen of the membranous structures of the inner ear of a mammal under conditions sufficient to bind an antibody in the biological sample to the antigen, wherein the antigen has an amino acid sequence selected from the group consisting of SEQ ID NO:1, SEQ ID NO:2 and SEQ ID NO:4; and
   (b) detecting the antibody bound to the antigens,
   wherein detection of the antibody bound to the antigen indicates a positive diagnosis of Meniere's disease.

2. The method of claim 1, wherein the antigen has a molecular weight of approximately 28 kD.

3. The method of claim 1, wherein the biological sample is a biological fluid from a human or animal having symptoms of an autoimmune inner ear disease.

4. The method of claim 1, wherein the biological sample is a biological fluid from a patient having symptoms of Meniere's disease.

5. The method of claim 1, wherein the biological fluid is serum.

6. The method of claim 1, wherein the amount of antibody in the biological sample is quantitated.

7. An assay kit aiding in the detection of Meniere's disease in a patient comprising:
   (a) an isolated antigen of the membranous structures of the inner ear of a mammal having an amino acid sequence selected from the group consisting of SEQ ID NO: 1, SEQ ID NO: 2 and SEQ ID NO: 4, wherein the antigen is reactive with an antibody in a biological fluid sample of an animal or human patient having symptoms of Meniere's disease and
   (b) means for detecting binding of the antibody to the antigen;
   wherein detection of the binding of the antibody to the antigen indicates that the patient has Meniere's disease.

8. The assay kit of claim 7, wherein the antigen is a recombinant protein or peptide or a synthesized protein or peptide.

* * * * *